US009983277B2

(12) United States Patent
Peterson

(10) Patent No.: US 9,983,277 B2
(45) Date of Patent: May 29, 2018

(54) CORE SAMPLE HOLDER

(71) Applicant: DAEDALUS INNOVATIONS LLC, Aston, PA (US)

(72) Inventor: Ronald W. Peterson, Media, PA (US)

(73) Assignee: DAEDALUS INNOVATIONS LLC, Aston, PA (US)

( * ) Notice: Subject to any disclaimer, the term of this patent is extended or adjusted under 35 U.S.C. 154(b) by 539 days.

(21) Appl. No.: 14/639,308

(22) Filed: Mar. 5, 2015

(65) Prior Publication Data

US 2015/0268314 A1 Sep. 24, 2015

Related U.S. Application Data

(60) Provisional application No. 61/968,694, filed on Mar. 21, 2014.

(51) Int. Cl.

| | |
|---|---|
| ***G01V 3/00*** | (2006.01) |
| ***G01R 33/30*** | (2006.01) |
| ***E21B 25/00*** | (2006.01) |
| ***E21B 47/00*** | (2012.01) |
| ***E21B 49/08*** | (2006.01) |

(52) U.S. Cl.

CPC ............ *G01R 33/305* (2013.01); *E21B 25/00* (2013.01); *E21B 47/0002* (2013.01); *E21B 49/081* (2013.01)

(58) Field of Classification Search

USPC .......................................................... 324/321

See application file for complete search history.

(56) References Cited

U.S. PATENT DOCUMENTS

| | | | | |
|---|---|---|---|---|
| 4,599,891 | A | 7/1986 | Brauer et al. | |
| 4,753,107 | A | 6/1988 | Reed et al. | |
| 4,827,761 | A | 5/1989 | Vinegar et al. | |
| 5,427,418 | A | 6/1995 | Watts | |
| 6,054,857 | A * | 4/2000 | Doty .................... | G01R 33/307 324/321 |
| 6,247,358 | B1 * | 6/2001 | dos Santos ............. | E21B 25/08 166/282 |

(Continued)

FOREIGN PATENT DOCUMENTS

| | | |
|---|---|---|
| CN | 103234888 | 8/2013 |
| WO | WO 2007/148214 | 12/2007 |
| WO | 20120082204 | 6/2012 |

*Primary Examiner* — Rodney Fuller

(74) *Attorney, Agent, or Firm* — Riverside Law LLP

(57) ABSTRACT

A sample holder that can withstand high pressures and temperatures is disclosed. The sample holder can be used to subject a geological sample to the same temperature and pressure that the sample would experience in its native underground environment. The sample holder provides a mechanism for hydrostatically confining the rock core sample to simulate the below ground pressure, while simultaneously allowing fluid to be directed through the core, as needed. The material used for the housing of the sample holder, specifically ceramic zirconia, and the mechanism by which the end fixtures are mounted in the housing, e.g., a square thread or modified square thread, allow for operation at higher pressures and temperatures than is offered by currently available systems. The sample holder can be used to analyze rock core samples via NMR spectroscopy or MRI.

19 Claims, 2 Drawing Sheets

100

49 48 51 52 33 50 34 35 53 21 22 40 54 14,15 12,13 55 59 58 56 57

32 39 37,38 2 3 4 5,7 6,8 16 1 19 36 23,24 25,26 18 27,28 29,30 31 20 47 17 46 10 11 41 9 43,44 45 42

(56) References Cited

U.S. PATENT DOCUMENTS

| | | | | |
|---|---|---|---|---|
| 9,038,450 | B2 * | 5/2015 | Pindiprolu | G01N 15/0826 73/152.07 |
| 2011/0050223 | A1 | 3/2011 | Balcom et al. | |
| 2013/0276554 | A1 * | 10/2013 | Matthews | E21B 25/005 73/864 |
| 2013/0342208 | A1 | 12/2013 | Mitchell et al. | |
| 2014/0044598 | A1 * | 2/2014 | Hu | B23G 1/02 422/68.1 |

* cited by examiner

CORE SAMPLE HOLDER

CROSS-REFERENCE TO RELATED APPLICATIONS

This application claims priority to U.S. patent application Ser. No. 61/968,694, filed Mar. 21, 2014, the entire contents of which are incorporated herein by reference.

BACKGROUND OF THE INVENTION

Rock core samples are extracted and analysed in a variety of industries. A rock core sample extracted from below ground can be used to obtain detailed information about the formation from which it originated. These samples are often analysed using imaging or spectroscopy techniques, such as magnetic resonance imaging (MRI) or nuclear magnetic resonance (NMR) spectroscopy. Typically, rock core samples are cylinders with a fixed diameter and flat parallel ends. Such samples are often subjected to high pressure and temperature in their native environment, which must be reproduced in the laboratory for optimal analysis.

In petrophysical research applications, a range of parameters can be measured from core samples during the relatively low-cost initial drilling stage to assist in the identification of "sweet spots" suitable for further exploration. The depth of wells used by the hydrocarbon industry continues to increase, leading to down-hole conditions having very high pressure and temperature. Accordingly, laboratories need instrumentation capable of reproducing these extreme conditions. Improvements in the correlation between data collected down-hole with that measured in a controlled laboratory setting can improve the targeting of "sweet spots" and can have a major impact on the economics of production.

Various types of sample holders can be used during analysis to attempt to simulate underground conditions. Preferably, core sample holders employed in the laboratory will apply pressure to the outside of the rock core at temperatures equivalent to the down-hole conditions. While under pressure, a secondary fluid that is detectable by the spectroscopic technique being used is typically forced into or through the rock core to allow the relevant parameters to be determined. Such sample cells are commonly called overburden cells since they apply pressure equivalent to the overburden experienced by the rock core underground.

There are several examples of sample core holders for the study of geologic cores in the literature. Sample core holders can be classified based on how pressure is applied to the core sample. A uniaxial core holder, or Hassler core holder, has a single inlet for the application of pressure to the core sample. This type of holder might be used to measure the pressure drop along the length of the core during flooding experiments. A biaxial core holder provides for two independent and isolated pressure sources. One source leads directly to and through the core and is typically the fluid of interest in analysis. The secondary source provides the confining pressure on the core to simulate the below ground conditions. This source acts on the core both axially, through the mounts that are in direct contact with the core faces, and radially around the core, through some type of compression sleeve. A triaxial core holder uses three independent pressure sources. One source is for delivering fluid through the core, one is for delivering pressure to the axial faces of the core sample, and another is for delivering pressure radially to the core (see, e.g., Brauer et al., U.S. Pat. No. 4,599,891; Reed et al., U.S. Pat. No. 4,753,107).

Some types of sample holders can be used with NMR spectroscopy, which requires materials that are non-magnetic and non-metallic, at least in the region surrounding the core sample (see, e.g., Vinegar et al., U.S. Pat. No. 4,827,761). For many modern, commercial NMR spectrometers there is a defined bore diameter of the instrument which cannot be easily altered. Therefore, most core holders are limited in the outside diameter, which is often not much larger than the geologic core sample. This limits the ratio of outside and inside diameters, which often largely defines the maximum pressure that can be reached. Accordingly, these limitations can result in the housing wall being relatively thin, which greatly reduces the ability of the housing to resist the internal pressure being applied. Further, fastening end plugs to the housing can be problematic if the housing wall is relatively thin.

Several methods have been devised to overcome these issues. One such method uses a large external clamping system that resembles a hydraulic press to hold the end plugs inside the housing. This method is reasonably successful, provided the end plugs can be very accurately aligned axially both with the housing and the direction of force applied by the clamps. Failure to achieve this alignment makes the system prone to leaks and can severely limit the maximum operating pressure. Another method uses pins applied radially through the wall of the housing to fasten the end plug to the housing. Although this type of sample holder may not suffer from the alignment issues of the previous method, it can be difficult to assemble and disassemble. Notably, current commercially available core holders for NMR make use of fiberglass or composite plastic as the material for at least the part of the housing surrounding the sample itself. These types of sample holders are useful for lower pressure, but are not capable of addressing the current pressure and temperature requirements of geological and petrophysical research.

Thus, there is a continuing need in the art for a core sample holder that can withstand the high temperatures and pressures associated with current petrophysical research, and that can also be used with NMR spectroscopy or MRI analysis. The present invention addresses this continuing need in the art.

SUMMARY OF INVENTION

The present invention relates to devices for holding rock core samples, or other types of samples, that can withstand high pressures and temperatures. In one embodiment, the device of present invention is a core sample holder for use with a nuclear magnetic resonance (NMR) spectrometer or magnetic resonance imaging (MRI) instrument, comprising: a top end plug, having a plug face; a bottom end plug, having a plug face; a hollow housing having two ends, wherein a portion of the ends are threaded to receive the top end plug and the bottom end plug, and wherein the housing comprises zirconia ceramic; a top mount having an outer surface and a face for contacting a sample; a bottom mount having an outer surface and a face for contacting a sample; a sleeve, having an inner surface and an outer surface, wherein the sleeve is connected to the top mount and the bottom mount; wherein a first chamber is formed inside the housing between the top mount face, the bottom mount face, and the inner surface of the sleeve, and wherein the first chamber is suitable for holding a sample; wherein a second chamber is formed inside the housing between the outer surface of the sleeve, the inner surface of the housing, the top end plug face, the bottom end plug face, the top mount outer surface, and the bottom mount outer surface when the top end plug and bottom end plug are secured to the threaded ends of the housing; and wherein the first chamber is sealed from the second chamber; at least one fluid transfer mechanism, for transferring a fluid into or out of the first chamber; and a means for increasing the pressure in the second chamber, wherein when the pressure is increased in the second chamber, axial and radial forces are applied to a sample in the first chamber.

In another embodiment, the present invention is a sample holder, comprising: a top end plug, comprising a sealing mechanism, a bottom end plug, comprising a sealing mechanism, and a hollow housing having two ends, wherein a portion of the ends are threaded to receive the top end plug and the bottom end plug, and wherein the thread angle of the load-bearing thread face of the threaded portions is less than about 14 degrees, wherein a chamber is formed within the housing when the top end plug and the bottom end plug are connected to the housing via the threaded portions, and wherein said chamber is sealed from the atmosphere.

In one embodiment, the housing of the device comprises zirconia ceramic. In one embodiment, the zirconia ceramic is Y-TZP zirconia.

In various embodiments, the device comprises threaded portions that allow the device to withstand high pressures. In one embodiment, the thread angle of the load-bearing thread face of the threaded portions is less than about 14 degrees. In one embodiment, the thread angle of the load-bearing thread face is approximately zero degrees. In one embodiment, the thread angle of the load-bearing thread face of the threaded portions is about 7 degrees or less, and the thread angle of the opposite thread face is about 45 degrees. In one embodiment, the threaded portions are a thread type selected from the group consisting of a square thread, buttress thread, V-threads, Acme thread, trapezoidal thread, knuckle thread, and pipe thread. In one embodiment, the threaded portions of the housing are on the inner surface of the housing. In one embodiment, the threaded portions of the housing are on the outer surface of the housing.

In various embodiments, the device comprises sealing mechanisms. In one embodiment, the device comprises a sealing mechanism for sealing the first chamber from the second chamber. In one such embodiment, the sealing mechanism is one or more o-rings connected to the top mount or bottom mount, wherein a seal is formed between the sleeve and the one or more o-rings. In one embodiment, the device comprises a sealing mechanism for sealing the second chamber from the surrounding environment. In one such embodiment, the sealing mechanism is one or more o-rings connected to the top plug or bottom plug.

The device of the present invention can be used in the analysis of various types of samples. In one embodiment, the sample is a rock core sample. In another embodiment, the sample is a liquid, gas, or combination thereof.

In various embodiments, the device comprises at least one fluid transfer mechanism. In one embodiment, the at least one fluid transfer mechanism is a tube inserted through the top plug or the bottom plug, wherein the tube has a conduit in communication with the first chamber. In one embodiment, the conduit is in communication with the first chamber via a second conduit in the top mount or bottom mount. In one embodiment, the tube is connected to the top plug or the bottom plug via a gland and collar. In one embodiment, the tube is connected to the top mount or the bottom mount via a gland and collar. In one embodiment, a fluid for analysis can be transferred to the first chamber via a first fluid transfer mechanism, through a sample in the first chamber, and out of the first chamber via a second fluid transfer mechanism. In one embodiment, the top mount face comprises a fluid distribution mechanism.

In one embodiment, at least a portion of the device, for example the second chamber, can be pressurized to a pressure in the range of about 5,000 to 35,000 psi. In one embodiment, the means for increasing the pressure in the second chamber is adding a pressurization fluid to the second chamber. In one embodiment, the pressurization fluid is added to the second chamber via a conduit in the top plug, and the pressurization fluid can flow out of the second chamber via a conduit in the bottom plug. In one embodiment, the device further comprises a tube having a conduit in communication with the conduit in the top plug, wherein the tube is connected to the top plug via a gland and collar. In one embodiment, the device further comprises a tube having a conduit in communication with the conduit in the bottom plug, wherein the tube is connected to the bottom plug via a gland and collar. In one embodiment, the sleeve of the device is connected to the top mount and the bottom mount via a friction fit.

BRIEF DESCRIPTION OF THE DRAWINGS

The following detailed description of various embodiments of the invention will be better understood when read in conjunction with the appended drawings. It should be understood, however, that the invention is not limited to the precise arrangements and instrumentalities of the embodiments shown in the drawings.

DETAILED DESCRIPTION

Figure 1:
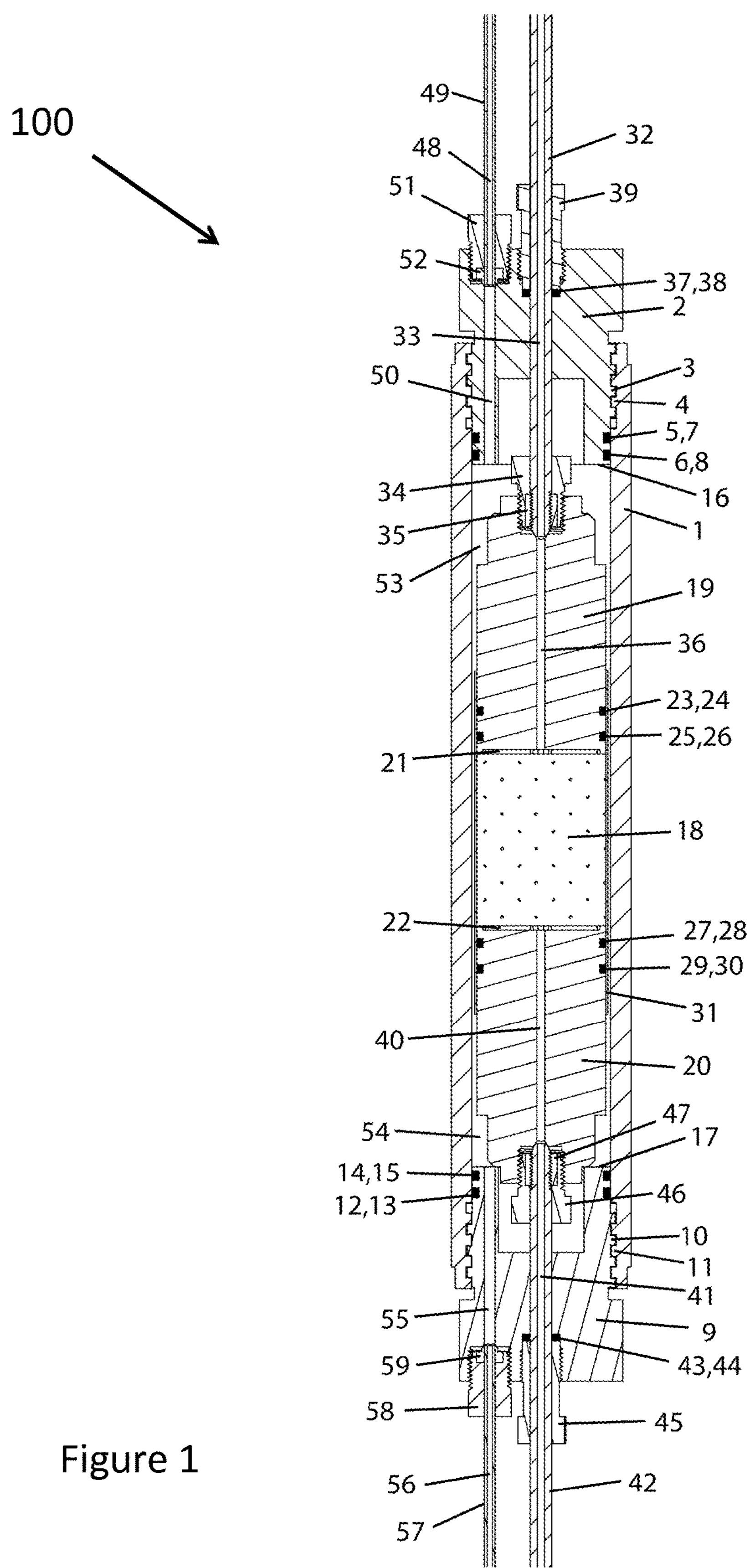
FIG. 1 is a schematic diagram of an exemplary embodiment of the sample holder of the present invention.

It is to be understood that the figures and descriptions of the present invention have been simplified to illustrate elements that are relevant for a clear understanding of the present invention, while eliminating, for the purpose of clarity, many other elements found in typical sample holders, or other devices and methods pertaining to the field of geologic core sample analysis. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles “a” and “an” are used herein to refer to one or to more than one (i.e., to at least one) of the grammatical object of the article. By way of example, “an element” means one element or more than one element.

“About” as used herein when referring to a measurable value such as an amount, a temporal duration, and the like, is meant to encompass variations of ±20%, ±10%, ±5%, ±1%, and ±0.1% from the specified value, as such variations are appropriate.

The term "zirconia ceramic" refers to any ceramic composition comprising zirconium oxide, including, but not limited to: tetragonal zirconia polycrystals, partially stabilized zirconia, fully stabilized zirconia, transformation toughened ceramics, zirconia toughened alumina, and transformation toughened zirconia. Further, a zirconia ceramic can comprise additional compounds, for example, but not limited to: magnesium oxide, calcium oxide, and yttrium oxide. For example, the zirconia ceramic of the present invention can be yttria-stabilized zirconia (YSZ), which when hot-isostatically pressed is also referred to in the art as yttria-tetragonal zirconia polycrystal (Y-TZP).

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Description

The devices and methods of the present invention relate to a holder for rock core samples, or other types of samples, that can withstand high pressures and temperatures. Rock core samples extracted from below ground can be used to obtain detailed information about the formation from which it originated. Such samples are often subjected to high pressure and temperature in their native environment. Accordingly, in one embodiment, the present invention is a sample core holder for geological samples where the sample can be subjected to high pressure and temperature to reproduce below ground conditions in the laboratory for optimal analysis. The present invention provides a mechanism for hydrostatically confining the rock core sample to simulate the below ground pressure, while simultaneously allowing fluid to be directed through the core, as needed. In one embodiment, the device of the present invention is a biaxial-type sample core holder. In another embodiment, the device is a triaxial-type sample core holder. In various embodiments, the material used for the housing of the sample holder, specifically ceramic zirconia, and the mechanism by which the end fixtures are mounted in the housing, e.g., a square thread or modified square thread, allow for operation at higher pressures and temperatures than is offered by currently available systems.

In one embodiment, the device of the present invention can be used to analyze rock core samples via NMR spectroscopy or MRI because the device can be made from non-magnetic materials, for example a ceramic material such as Y-TZP zirconia. Further, an advantage of the device for use with NMR or MRI is that it can comprise a threaded housing and plugs with the maximum outer diameter of the device defined by the housing diameter surrounding the core sample. Therefore, the sample holder of the present invention can fit within a NMR or MRI instrument without the need to modify the instrument. Further still, the present invention relates to the use of a thread design that minimizes radial pressure on a thin-walled housing, and thus greatly enhances the operating performance pressure of the sample holder.

Referring now to FIG. 1, a preferred embodiment of the core holder of the present invention is shown. Core holder 100 comprises a cylindrical housing 1 having openings on both ends. A portion of the inner surface of the housing is threaded at both ends, i.e., portions 4 and 11, to accommodate a top plug 2 and a bottom plug 9. The thread profile on the housing and also the thread profiles of top plug 2 and bottom plug 9 are of a modified square form. High pressure is typically applied to the plug faces 16 and 17 when core holder 100 is used. For a thread form other than a modified square form, wherein the planar load bearing surface deviates significantly from a plane perpendicular to the axis of force, the operational pressure can be sufficient to cause failure of the housing wall and severely limit the pressure tolerance of the sample holder. However, a square thread form minimizes radial pressure and thus maximizes the utility and performance of the device of the present invention. In one embodiment, housing 1 comprises a zirconia ceramic, such as Y-TZP zirconia. In another embodiment, the housing can comprise any other type of material that is non-magnetic and can be made with a threaded portion having a square-type thread.

The threaded top plug 2 and threaded bottom plug 9 can be manufactured from a non-magnetic metal with a coefficient of thermal expansion that will not cause fracturing of the zirconia housing at a relatively high operating pressure and temperature, for example a pressure in the range of about 5,000 to 35,000 psi and/or a temperature of 300° C. or more. Elastomer o-rings 5 and 6 can fit into circumferential grooves 7 and 8 in top plug 2 and are compressed into position to form a high pressure seal against interior wall of housing 1. This mechanism of sealing can be the same for bottom plug 9 with the elastomer o-rings 12 and 14 fitting into groove 13 and 15 on bottom plug 9 to form the high pressure seal.

A geologic core sample 18 is placed between high temperature-stable mounts 19 and 20, i.e., top mount 19 and bottom mount 20. Distribution faces 21 and 22 of mounts 19 and 20 are patterned to deliver fluid relatively uniformly to the faces of core 18 that are in contact with mounts 19 and 20. When sample holder 100 is used during an analysis, a first fluid can be delivered to the core sample 18, while a second fluid can be used to generate an overburden pressure on the core sample, i.e., the radial and axial pressure imposed on the core sample to mimic natural geologic conditions. The first fluid and the core sample must generally be isolated from the second fluid used to generate the overburden pressure. Accordingly, the sample holder comprises a mechanism for isolating the first fluid and second fluid, which is described below. In addition, the device of the present invention comprises a fluid transfer mechanism for transferring the first fluid to and through core sample 18, which is also described below.

The first fluid is transferred into housing 1, and eventually to core sample 18, via a conduit 33 in a tube 32. Conduit 33 is in communication with a conduit 36 in mount 19. The first fluid can flow through conduit 33 into conduit 36 in mount 19. The first fluid can then continue through conduit 36 and into core sample 18 via distribution face 21. Tube 32 is inserted through an opening in top plug 2 and is secured to top mount 19 via a high pressure gland 34 and collar 35. Gland 34 and collar 35 can be any commercially available gland and collar, as would be understood by a person skilled in the art. Further, a high pressure seal between tube 32 and top plug 2 is created by a polytetrafluoroethylene o-ring 37 placed into a recessed area 38 in top plug 2. O-ring 37 is compressed by a piston plug 39 which forces o-ring 37 against the outer wall of tube 32. The seal between tube 32 and top plug 2 is dynamic in that it allows tube 32 to move axially with the application of pressure to the faces of top mount 19. The allowance for axial movement is necessary because geologic core samples can compress or stretch at high pressures. Accordingly, mount 19 must be allowed to move relatively freely to maintain contact with the core.

O-rings 23, 25, 27, and 29 are placed within grooves 24, 26, 28, and 30 on mounts 19 and 20. These o-rings are compressed into a high pressure seal configuration by a fluorinated ethylene propylene sleeve 31. In one embodiment, sleeve 31 connects to mounts 19 and 20 via a friction fit. In one embodiment, sleeve 31 is heat shrinkable. As describe below, the overburden pressure is applied to core sample 18 via a second fluid. The first and second fluids are isolated from each other in part by sleeve 31, which is connected to both top mount 19 and bottom mount 20, thereby forming a chamber for holding core sample 18. This chamber, i.e., the first chamber, is sealed from the chamber that holds the second fluid, i.e., the second chamber, by the combination of sleeve 31 and o-rings 23, 25, 27, and 29. In addition, the overburden pressure created by the second fluid assists in maintaining the high pressure sealing integrity of the seal between sleeve 31 and mounts 19 and 20.

Fluid that has passed through core sample 18 can then pass through the fluid collection face 22 into conduit 40 in bottom mount 20. The fluid can then flow into conduit 41 in tube 42 and out of sample holder 100. A high pressure gland 46 and collar 47 is used to connect tube 42 to bottom mount 20. A high pressure seal between tube 42 and bottom plug 9 is created by a polytetrafluoroethylene o-ring 43 placed into a recessed area 44 in bottom plug 9. O-ring 43 is compressed by the piston plug 45 which forces o-ring 43 against the outer wall of tube 42. Similar to tube 32, this seal is also dynamic in that it will allow mount 20 to move during use of the core holder 100. However, mount 20 will generally be placed directly against bottom plug 9 during the core holder assembly so it will most usually be in a static position during operation.

The fluid that provides the axial and radial overburden pressure to the geologic core, i.e., the second fluid, is delivered through conduit 48 in tube 49. The fluid then passes through conduit 50 in top plug 2 and into the internal chamber 53 within core holder 100. A seal is made between tube 49 and top plug 2 using a high pressure gland 51 and collar 52. The fluid that enters chamber 53 can pass freely around core sample 18 and sleeve 31 to chamber 54 below core sample 18. The fluid thus delivers radial pressure to core sample 18 through sleeve 31. Therefore, the second chamber comprises chambers 53 and 54, and also the space between the outer surface of sleeve 31 and the inner surface of housing 1. The fluid can then pass from chamber 54 into conduit 55 in bottom plug 9, through conduit 55 into conduit 56 in tube 57, and out of core holder 100. A seal between tube 57 and bottom plug 9 is created using a high pressure gland 58 and collar 59.

The core mounting procedure is generally performed prior to inserting the sample into sample holder 100. For example, core sample 18 is placed on bottom mount 20. Top mount 19 is placed on core sample 18, and then sleeve 31 is placed around top mount 19, core sample 18, and bottom mount 20, so that sleeve 31 covers o-rings 23, 25, 27, and 29. This assembly can be subjected to heat to shrink the sleeve 31 and compress the o-rings 23, 25, 27, and 29. The mounted core sample is then placed inside housing 1, wherein end plugs 2 and 9 are then secured to housing 1. The components of sample holder 100 can be made from various materials. For example, in a preferred embodiment, sleeve 31 comprises fluorinated ethylene propylene. In a preferred embodiment, tubes 32, 42, 49, and 57 comprise stainless steel. In a preferred embodiment, the o-rings comprise polytetrafluoroethylene. However, the materials of construction of the various components of the present invention are not limited to any specific materials described herein, and each component can comprise any material, as would be understood by a person skilled in the art, based on the function of the component and the characteristics required for proper operation of that component.

The embodiment shown in FIG. 1, and described above, is a biaxial sample holder. However, in another embodiment, the sample holder of the present invention can have a triaxial design. In such an embodiment, the sample holder can comprise additional components necessary for applying a third fluid inside the housing, wherein the third fluid is prevented from commingling with the first fluid and the second fluid. As would be understood by a person skilled in the art, the first fluid can be applied directly to and through the core sample, the second fluid can be used to apply axial force to the core sample, and the third fluid can be used to apply radial force to the core sample.

Figure 2:
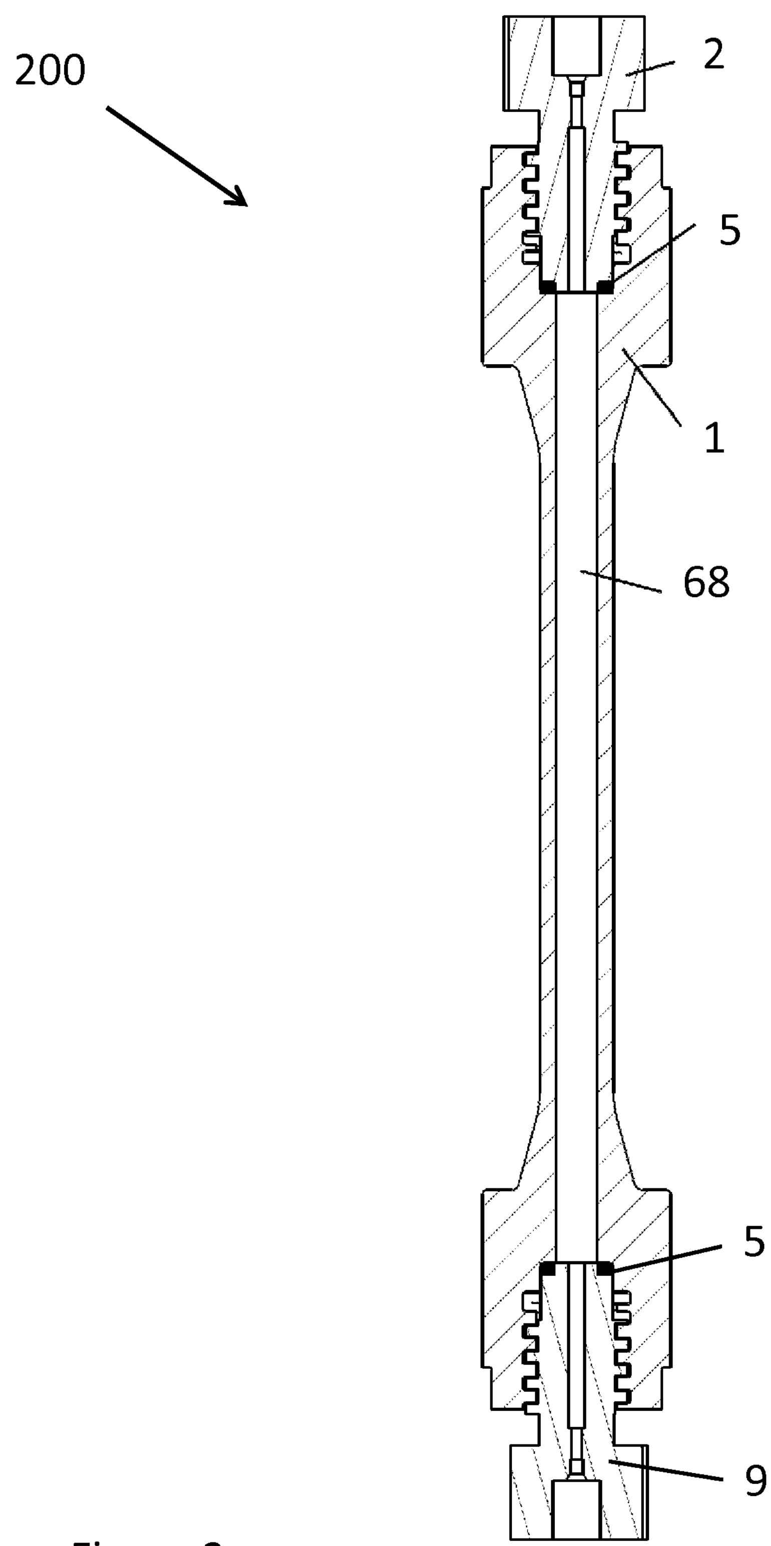
FIG. 2 is a schematic diagram of an alternative embodiment of the sample holder of the present invention.

Referring now to FIG. 2, another embodiment of the sample holder of the present invention is shown. Sample holder 200 comprises a chamber 68 for holding a sample. In one embodiment, chamber 68 can be used to hold a sample other than a rock core sample, for example a liquid sample, gas sample or a combination thereof. Sample holder 200 comprises a housing 1 and end plugs 2 and 9, wherein chamber 68 is sealed from the surrounding environment via o-rings 5. In one embodiment, end plugs 2 and 9 can be secured to housing 1 via a modified square thread design. Either or both plugs 2 and 9 can be connected to conduits to allow the introduction of samples, pressurization of samples already present, or to allow fluid flow through the housing. Further, in one embodiment, housing 1 can comprise ceramic zirconia. Accordingly, sample holder 200 can be used to analyze a sample at high pressure using NMR or MRI.

The primary advantages of the sample holder of the present invention over currently available core sample holders is the material of construction of the housing and the mechanism for fixing the end caps, i.e., the top and bottom plugs, in the housing. In a preferred embodiment, the housing of the sample holder of the present invention comprises ceramic zirconia. Ceramic zirconia provides a significant improvement over materials such as fiberglass because it allows complex shapes such as threads to be readily formed without significant loss in strength. When compared to composite plastics, the strength properties of ceramic zirconia are nearly an order of magnitude greater, which allows for a more flexible design than currently available core holders, while at the same time extending the operating capabilities of the core holder.

The thread mechanism for restraining the end plugs in the housing of the present invention is made possible in part because of the use of ceramic zirconia as a material of construction. This thread mechanism eliminates many problems associated with currently available sample holding devices. The profile of the core holder housing thread provides a critical advantage of the present invention.

Referring again to FIG. 1, the area in housing 1 between the plug faces 16 and 17 is the zone of the core holder subjected to direct hydrostatic pressure during operation. Therefore, the threaded portions of housing 1 are outside this pressure zone during operation, and only experience forces in an axial direction. In general, using a standard numerical analysis known to a person skilled in the art, if the housing wall in the pressure zone is sufficiently thick, and also the combined thickness of the housing wall cross section in the threaded portion is sufficiently thick to resist the axial force for a given pressure rating, then the housing would be suitable for that pressure rating. Such an analysis would generally be expected to find that the force required to shear the threaded section of the housing is several times greater than the pressure resistance of the housing wall in the pressure zone. However, in practice, it has been observed that the failure pressure is highly dependent on the thread profile. Further, the pressure required to shear the threaded section can be much less than the pressure required to fracture the housing in the pressure zone. For example, fabricated models with thread profiles other than a modified square profile have been found to fracture at relatively low pressures. Accordingly, a thread profile that minimizes the radial pressure applied to the threaded housing portions, e.g., a modified square thread profile, performs best.

There are several standard thread profiles known in the art, with each thread offering a load-bearing face at a specific angle to the axial direction of force. For the three most common thread styles, V-threads, trapezoidal threads such as Acme, and square threads, the angle between threads or the thread angle is about 60°, 29°, and zero, respectively. These thread angles correspond to a load-bearing plane that is offset about 60°, 75.5°, and 90°, respectively, from the direction of force. The tolerance to the axial force, and thus the overall pressure tolerance of the thread design, increases as the thread angle approaches zero.

It is contemplated herein that the use of the terms “face” or “plane” with respect to threads, thread profiles, and the like can refer to a surface that may not be flat. For example, in one embodiment, the load-bearing face may be slightly concave or curved. Further, in one embodiment, the corners or edges of the threads can be curved or rounded. For example, in embodiments of the device of the present invention that are made from ceramic, the thread corners or edges can be rounded as a result of ceramic machining techniques typically used in manufacturing. However, in some embodiments, the thread faces of the device can be substantially or completely flat, i.e., the thread faces can have smooth, even surfaces. Accordingly, as would be understood by a person skilled in the art, the thread faces and/or the edges of the thread faces of the device of the present invention can be curved, slightly curved, or flat depending on the material of construction and/or the fabrication techniques used.

To compare the performance of various thread profiles, several housing models were fabricated with consistent outside diameter and inside diameter in the pressure zone, and the minimum wall thickness in the threaded section was the same. Only the thread profile was varied. In this direct comparison, the housing with Acme threads withstood pressures 50% higher than one with V-threads. Further, the housing with square threads withstood pressure 50% higher than one with Acme threads.

Although square threads performed best in the fabricated models, the preferred embodiment of the present invention is not a standard square thread design wherein the thread groove and height are equivalent. Such a design is not generally practical due to dimensional constraints that make the wall thickness in the threaded section too thin if conventional manufacturing techniques are followed. Therefore, the preferred thread design of the present invention is a modified square design, wherein the angle of the thread load-bearing face upon which the axial force is directed is perpendicular or nearly so to the axis of force. For example, in one embodiment, the thread angle of the threaded housing portions can be in the range of about 0 to 14 degrees, i.e., the load-bearing thread face is perpendicular or nearly perpendicular to the housing wall.

In other embodiments, a person skilled in the art could use alternative thread designs that can further improve the overall pressure tolerance of the housing. An example of such a thread design is a buttress thread, which resembles a saw tooth. This design combines the near perpendicular angle of the thread load-bearing face with the face opposite the plane of force slanted at 45°. For example, in one embodiment, the thread angle of the load-bearing thread face of the threaded housing portions is about 7 degrees or less, i.e., the angle of the load-bearing face with respect to the housing wall is nearly perpendicular, and the thread angle of the opposite thread face is about 45 degrees, i.e., the opposite thread face forms an angle of about 45 degrees with the housing wall. Such a design can provide the same minimization of the radial pressure on the housing at the point of contact plus a wider thread root, and thus overall higher thread strength, than the modified square design described herein. This design can be useful where individual thread shear, rather than the housing wall shear, becomes the dominating limiting factor in overall performance.

An important objective of the present invention is to provide for a self-contained pressure vessel that can be inserted into modern wide-line NMR spectrometers without modification to the instrument. This requires that the maximum outer diameter of the core holder section that will be inserted into the NMR probe cannot exceed the inner diameter of the probe. To insert the core sample, at least one end of the housing must be sufficiently large to accommodate the sample, but it does not require that both ends be able to do so. In such an embodiment of the present invention, the entire core holder can be inserted into the NMR probe, hence the maximum diameter is defined by the region surrounding the sample and both ends of the housing allow the core sample to pass.

There are variations on the sample holder of the present invention that would be readily understood by an artisan experienced with this type of technology. In one embodiment, the threaded portion of the housing can be on the outer surface of the housing instead of the inner surface. Accordingly, a cap can be used instead of a plug to seal the housing from the surrounding environment. In one embodiment, one end of the housing can be larger than the NMR probe diameter, wherein the wider end of the housing would remain outside the probe to meet other application objectives. Further, in various embodiments, the sample holder of the present invention can be used to analyze samples other than geologic core samples, for example a liquid, gas or a combination thereof. Further still, although the sample holder of the present invention has been described in various embodiments related to NMR or MRI analysis, a person skilled in the art would understand that in other embodiments, the sample holder can be used in applications where high pressure and temperature tolerance is required, but non-magnetic materials are not required.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A core sample holder for use with a nuclear magnetic resonance (NMR) spectrometer or magnetic resonance imaging (MRI) instrument, comprising:

a top end plug, having a plug face;

a bottom end plug, having a plug face;

a hollow housing having two ends, wherein a portion of the ends are threaded to receive the top end plug and the bottom end plug, and wherein the housing comprises zirconia ceramic;

a top mount having an outer surface and a face for contacting a sample;

a bottom mount having an outer surface and a face for contacting a sample;

a sleeve, having an inner surface and an outer surface, wherein the sleeve is connected to the top mount and the bottom mount;

wherein a first chamber is formed inside the housing between the top mount face, the bottom mount face, and the inner surface of the sleeve, and wherein the first chamber is suitable for holding a sample;

wherein a second chamber is formed inside the housing between the outer surface of the sleeve, the inner surface of the housing, the top end plug face, the bottom end plug face, the top mount outer surface, and the bottom mount outer surface when the top end plug and bottom end plug are secured to the threaded ends of the housing; and wherein the first chamber is sealed from the second chamber;

at least one fluid transfer mechanism, for transferring a fluid into or out of the first chamber; and a means for increasing the pressure in the second chamber, wherein when the pressure is increased in the second chamber, axial and radial forces are applied to a sample in the first chamber.

2. The sample holder of claim 1, wherein the thread angle of the load-bearing thread face of the threaded portions is less than about 14 degrees.

3. The sample holder of claim 2, wherein the thread angle of the load-bearing thread face is approximately zero degrees.

4. The sample holder of claim 1, wherein the thread angle of the load-bearing thread face of the threaded portions is about 7 degrees or less, and the thread angle of the opposite thread face is about 45 degrees.

5. The sample holder of claim 1, wherein the threaded portions of the housing are a thread type selected from the group consisting of a square thread, buttress thread, V-threads, Acme thread, trapezoidal thread, knuckle thread, and pipe thread.

6. The sample holder of claim 1, wherein at least one of the threaded portions of the housing is on the inner surface of the housing.

7. The sample holder of claim 1, wherein at least one of the threaded portions of the housing is on the outer surface of the housing.

8. The sample holder of claim 1, further comprising a sealing mechanism for sealing the first chamber from the second chamber.

9. The sample holder of claim 1, further comprising a sealing mechanism for sealing the second chamber from the surrounding environment.

10. The sample holder of claim 1, wherein the second chamber can be pressurized to a pressure in the range of about 5,000 to 35,000 psi.

11. The sample holder of claim 1, wherein the at least one fluid transfer mechanism is a tube inserted through the top plug or the bottom plug, wherein the tube has a conduit in communication with the first chamber.

12. The sample holder of claim 11, wherein the conduit is in communication with the first chamber via a second conduit in the top mount or bottom mount.

13. The sample holder of claim 11, wherein the tube is connected to the top plug or the bottom plug via a gland and collar.

14. The sample holder of claim 11, wherein the tube is connected to the top mount or the bottom mount via a gland and collar.

15. The sample holder of claim 11, wherein a fluid for analysis can be transferred to the first chamber via a first fluid transfer mechanism, through a sample in the first chamber, and out of the first chamber via a second fluid transfer mechanism.

16. The sample holder of claim 1, wherein the top mount face comprises a fluid distribution mechanism.

17. The sample holder of claim 1, wherein the means for increasing the pressure in the second chamber is adding a pressurization fluid to the second chamber; the pressurization fluid is added to the second chamber via a conduit in the top plug; and the pressurization fluid can flow out of the second chamber via a conduit in the bottom plug.

18. The sample holder of claim 17, further comprising a tube having a conduit in communication with the conduit in the top plug, wherein the tube is connected to the top plug via a gland and collar.

19. The sample holder of claim 17, further comprising a tube having a conduit in communication with the conduit in the bottom plug, wherein the tube is connected to the bottom plug via a gland and collar.

* * * * *